United States Patent
Biber et al.

(10) Patent No.: US 9,851,423 B2
(45) Date of Patent: Dec. 26, 2017

(54) PATIENT-ADAPTIVE $B_0$ HOMOGENIZATION OF MR SYSTEMS USING DIFFERENT TYPES OF SHIM COILS

(71) Applicants: Stephan Biber, Erlangen (DE); Ralf Ladebeck, Erlangen (DE)

(72) Inventors: Stephan Biber, Erlangen (DE); Ralf Ladebeck, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 565 days.

(21) Appl. No.: 14/464,073

(22) Filed: Aug. 20, 2014

(65) Prior Publication Data
US 2015/0054510 A1    Feb. 26, 2015

(30) Foreign Application Priority Data
Aug. 21, 2013 (DE) .................. 10 2013 216 529

(51) Int. Cl.
*G01R 33/3875* (2006.01)
*A61B 5/05* (2006.01)
(Continued)

(52) U.S. Cl.
CPC .......... *G01R 33/3875* (2013.01); *A61B 5/055* (2013.01); *A61B 5/0522* (2013.01); *G01R 33/445* (2013.01)

(58) Field of Classification Search
CPC .......... G01R 33/3875; G01R 33/34046; G01R 33/341; G01R 33/30; G01R 33/3415;
(Continued)

(56) References Cited

U.S. PATENT DOCUMENTS

| 5,173,661 A | 12/1992 | Knuttel et al. |
| 5,587,658 A * | 12/1996 | Sukumar ............ G01R 33/3875 324/307 |

(Continued)

FOREIGN PATENT DOCUMENTS

| CN | 102053233 A | 5/2011 |
| CN | 102331566 A | 1/2012 |

(Continued)

OTHER PUBLICATIONS

German Office Action dated Feb. 21, 2014 for corresponding German Patent Application No. DE 10 2013 216 529.3 with English translation.
(Continued)

*Primary Examiner* — Clayton E Laballe
*Assistant Examiner* — Ruifeng Pu
(74) *Attorney, Agent, or Firm* — Lempia Summerfield Katz LLC

(57) ABSTRACT

The embodiments relate to methods and to magnetic resonance tomography systems having a shim system, where the shim system includes at least one global shim coil in an area surrounding the bore of the magnetic resonance tomography system, and where the shim system includes a local shim coil in a local coil of the magnetic resonance tomography system with a shim controller, where the shim controller embodied to define shim currents for the global shim coil and for the local shim coil.

27 Claims, 1 Drawing Sheet

(51) Int. Cl.
*A61B 5/055* (2006.01)
*G01R 33/44* (2006.01)

(58) Field of Classification Search
CPC .... G01R 33/385; G01R 33/387; G01R 33/44; G01R 33/5607; G01R 33/5608; G01R 33/5613; G01R 33/56563; G01R 33/5659; G01R 33/3657; G01R 33/42; G01R 33/543; A61B 5/055; A61B 2560/0214; A61B 2576/026; A61B 5/00472; A61B 5/6814; A61B 5/6822; G06T 2207/10088; G06T 5/009; G06F 3/1462
See application file for complete search history.

(56) References Cited

U.S. PATENT DOCUMENTS

| | | | |
|---|---|---|---|
| 5,602,480 A * | 2/1997 | Onodera | G01R 33/3875 324/309 |
| 5,650,724 A | 7/1997 | Yamagata | |
| 7,215,123 B2 * | 5/2007 | Axel | G01R 33/3875 324/318 |
| 7,414,401 B1 | 8/2008 | Lvovsky | |
| 2004/0183536 A1 * | 9/2004 | Huang | G01R 33/3875 324/320 |
| 2005/0127914 A1 | 6/2005 | Eberler et al. | |
| 2005/0154291 A1 * | 7/2005 | Zhao | G01R 33/56375 600/410 |
| 2007/0241755 A1 * | 10/2007 | Ikedo | G01R 33/3875 324/320 |
| 2008/0088306 A1 * | 4/2008 | Dewdney | A61B 5/055 324/309 |
| 2008/0088307 A1 * | 4/2008 | Dewdney | G01R 33/3875 324/309 |
| 2008/0129298 A1 * | 6/2008 | Vaughan | G01R 33/583 324/322 |
| 2009/0322330 A1 * | 12/2009 | Adachi | G01R 33/5659 324/309 |
| 2010/0244823 A1 * | 9/2010 | Abe | A61B 5/055 324/309 |
| 2011/0109315 A1 | 5/2011 | Biber et al. | |
| 2012/0074940 A1 * | 3/2012 | Kimura | A61B 5/055 324/314 |
| 2012/0139538 A1 | 6/2012 | Schmidt et al. | |
| 2012/0323113 A1 | 12/2012 | Biber | |
| 2013/0015854 A1 * | 1/2013 | Adalsteinsson | G01R 33/56563 324/307 |
| 2013/0127468 A1 | 5/2013 | Biber | |
| 2013/0134978 A1 | 5/2013 | Biber | |
| 2013/0165768 A1 | 6/2013 | Biber | |
| 2013/0193968 A1 | 8/2013 | Biber | |
| 2013/0207655 A1 | 8/2013 | Biber | |
| 2014/0062475 A1 * | 3/2014 | Koch | G01R 33/56563 324/309 |
| 2014/0327440 A1 * | 11/2014 | Nakanishi | A61B 5/055 324/309 |
| 2015/0077107 A1 * | 3/2015 | Sharp | G01R 33/56563 324/309 |
| 2015/0301135 A1 * | 10/2015 | Biber | G01R 33/3875 324/307 |
| 2015/0355306 A1 * | 12/2015 | Stemmer | G01R 33/56563 324/309 |
| 2015/0362578 A1 * | 12/2015 | Biber | G01R 33/3875 324/309 |
| 2016/0011287 A1 * | 1/2016 | Dewdney | G01R 33/3875 324/309 |
| 2016/0139220 A1 * | 5/2016 | Liu | G01R 33/56563 382/131 |
| 2016/0274202 A1 * | 9/2016 | Stemmer | A61B 5/055 |
| 2016/0274205 A1 * | 9/2016 | Stemmer | G01R 33/3875 |

FOREIGN PATENT DOCUMENTS

| | | |
|---|---|---|
| CN | 103169473 A | 6/2013 |
| DE | 3937150 A1 | 5/1991 |
| DE | 19741748 A1 | 12/1998 |
| DE | 10314215 B4 | 11/2006 |
| DE | 102011077724 A1 | 12/2012 |
| DE | 102011080275 A1 | 2/2013 |
| DE | 102011081039 A1 | 2/2013 |
| DE | 102011086658 B3 | 3/2013 |
| DE | 102011087485 B3 | 5/2013 |
| JP | H0779942 A | 3/1995 |
| JP | 2011229632 A | 11/2011 |

OTHER PUBLICATIONS

Michael Wendt, PhD, "Second Order Shimming of High Field Magnets," Siemens Medical Solutions USA, Inc., pp. 1-4, Oct. 14, 2002.
Korean Office Action for Korean Application No. 10-2014-00107158, dated Mar. 13, 2017, with English Translation.
Chinese Office Action for Chinese Patent Application No. 201410414924.6 dated Dec. 12, 2016, with translation.

* cited by examiner

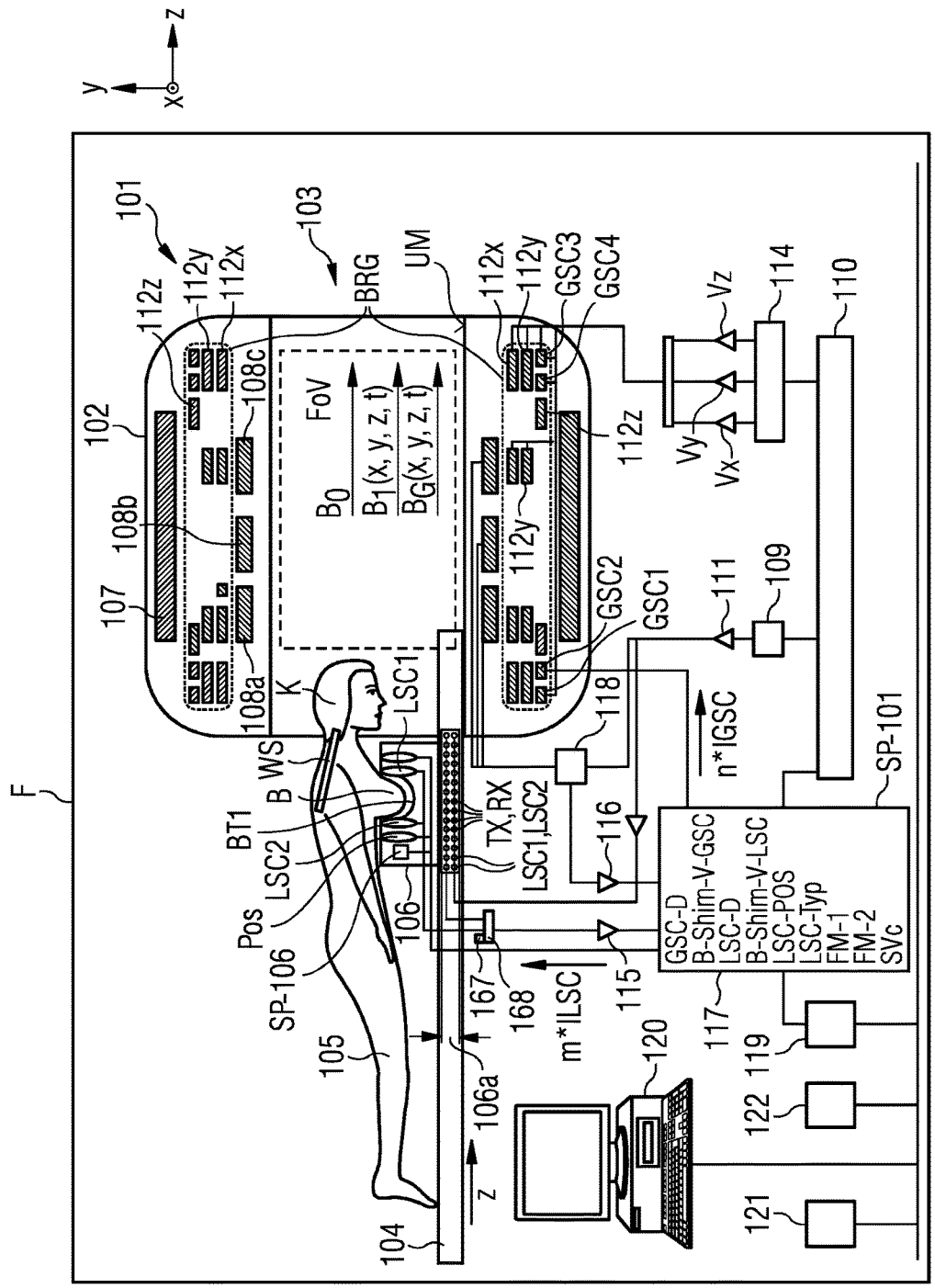

PATIENT-ADAPTIVE $B_0$ HOMOGENIZATION OF MR SYSTEMS USING DIFFERENT TYPES OF SHIM COILS

CROSS-REFERENCE TO RELATED APPLICATIONS

This application claims the benefit of DE 10 2013 216 529.3, filed on Aug. 21, 2013, which is hereby incorporated by reference in its entirety.

TECHNICAL FIELD

The embodiments relate to methods and devices for magnetic resonance tomography.

BACKGROUND

Magnetic Resonance Tomographs (MRTs) for examination of objects or patients by magnetic resonance tomography are known, for example, from DE 103 14 215 B4, DE 10 2011 080 275, DE 10 2011 087 485, DE 10 2011 086 658, DE 10 2011 081 039, and DE 10 2011 077 724.

SUMMARY

The scope of the present invention is defined solely by the appended claims and is not affected to any degree by the statements within this summary. The present embodiments may obviate one or more of the drawbacks or limitations in the related art.

The embodiments relate to methods and to magnetic resonance tomography systems having a shim system, where the shim system includes at least one global shim coil in an area surrounding the bore of the magnetic resonance tomography system, and where the shim system includes a local shim coil in a local coil of the magnetic resonance tomography system with a shim controller, where the shim controller embodied to define shim currents for the global shim coil and for the local shim coil.

BRIEF DESCRIPTION OF THE DRAWINGS

FIG. 1 depicts one embodiment of a schematic diagram of the MRT system.

DETAILED DESCRIPTION

FIG. 1 depicts an imaging magnetic resonance device MRT 101 (located in a screened room or Faraday cage F) with a whole-body coil 102, here with a tubular chamber 103, into which a patient couch 104 with a body, e.g., of an object under examination 105 (e.g., of a patient) (with or without local coil arrangement 106) may be moved in the direction of the arrow z, in order to generate images of the patient 105 using an imaging method. A local coil arrangement 106 is disposed on the patient here, with which, in a local area (also referred to as the "Field of View" or FoV) of the MRT, images of a part area of the body 105 may be generated in the FoV. Signals of the local coil arrangement 106 may be evaluated by an evaluation device (168, 115, 117, 119, 120, 121, etc.) of the MRT 101 able to be connected to the local coil arrangement 106 via coaxial cable or wirelessly (e.g., converted into images, stored or displayed).

In order to examine a body 105 (an examination object or a patient) with a Magnetic Resonance Tomograph MRT by magnetic resonance imaging, different magnetic fields matched as exactly as possible to one another in their temporal and spatial characteristics are beamed into the body 105. A strong magnet (often a cryomagnet 107) in a measurement cabin, here with a tunnel-shaped opening 103, creates a statically-strong main magnetic field $B_0$, which amounts to between 0.2 Tesla and 3 Tesla or even more, for example. A body to be examined 105 is supported on a patient couch 104 and moved into a roughly homogeneous area of the main magnetic field B0 in the FoV. The nuclear spins of atomic nuclei of the body 105 are excited via magnetic radio-frequency excitation pulses B1(x, y, z, t), which are beamed in here via a radio-frequency antenna depicted here as a body coil 108 (e.g., multipart=108a, 108b, 108c) and/or, in certain embodiments, a local coil arrangement. Radio-frequency excitation pulses are created by a pulse generation unit 109, for example, which is controlled by a pulse sequence control unit 110. After amplification by a radio-frequency amplifier 111, the pulses are conveyed to the radio-frequency antenna 108. In certain embodiments, more than one pulse generation unit 109, more than one radio-frequency amplifier 111, and a number of radio frequency antennas 108a, b, c are used in a magnetic resonance device 101.

The magnetic resonance device 101 also has gradient coils 112x, 112y, 112z, with which, during a measurement, magnetic gradient fields $B_G$(x, y, z, t) are beamed in for selective slice excitation and for local encoding of the measurement signal. The gradient coils 112x, 112y, 112z are controlled by a gradient coil control unit 114 (and, in certain embodiments, via amplifiers Vx, Vy, Vz) that, like the pulse generation unit 109, has a connection to the pulse sequence control unit 110.

Signals sent out by the excited nuclear spin (of the atomic nuclei in the examination object) are received by the body coil 108 and/or at least one local coil arrangement 106. The signals are also amplified by assigned radio-frequency amplifier 116 and further processed and digitized by a receive unit 117. The recorded measurement data is digitized and stored as complex numerical values in a k-space matrix. From the k-space matrix occupied by values, an associated MR image is able to be reconstructed by a multidimensional Fourier transformation.

For a coil that may be operated both in transmit and also in receive mode, such as the body coil 108 or a local coil 106, for example, the correct signal forwarding is regulated by an upstream transceiver switch 118.

An image processing unit 119 creates an image from the measurement data that may be displayed to a user and/or stored in a memory unit 121 via an operator console 120. A central processing unit 122 controls the individual system components.

In MR tomography, images with a high signal-to-noise ratio ("SNR") are nowadays may be recorded with local coil arrangements (e.g., coils, local coils). These are antenna systems that are attached in the immediate vicinity at (e.g., anterior), below (e.g., posterior), on the body 105, or in the body 105. In an MR measurement, the excited nuclei induce a voltage in the individual antennas of the local coils that is amplified with a low-noise preamplifier (e.g., LNA, preamp) and is forwarded to the receiver electronics. To improve the signal-to-noise ratio even with high-resolution images, so-called high field systems (e.g., 1.5 T-12 T or more) are used. If more individual antennas may be connected to an MR receive system than there are receivers present, a switching matrix (also referred to as an RCCS) is installed between receiver antennas and receivers, for example. The switching matrix routes the currently active receive channels (e.g., the channels that currently lie in the FoV of the magnet) to the existing receivers. This makes it possible to connect more coil elements than there are receivers present since, for whole-body coverage, only those coils that are located in the FoV or in the homogeneity volume of the magnet have to be read out.

An antenna system, which may include of one or a number of antenna elements as an array coil (e.g., coil elements), may be referred to as a local coil arrangement 106, for example. These individual antenna elements are embodied, for example, as loop antennas (e.g., loops), butterfly, flex coils, or saddle coils. A local coil arrangement includes, for example, coil elements, a preamplifier, further electronics (e.g., sheath current filters etc.), a housing, supports, and mostly a cable with plug through which the arrangement is connected to the MRT system. A receiver 168 attached on the system side filters and digitizes a signal received from a local coil 106, (e.g., wirelessly, etc.), and transfers the data to a digital signal processing device. From the data obtained by a measurement, the processing device derives an image or a spectrum and makes it available to the user, for example, for subsequent diagnosis by the user and/or for storage.

FIG. 1 also depicts methods and devices for the shim.

A distinction may be made between the following two types of shim coils in particular. A first type of shim coil is a Global Shim Coil (GSC, also referred to as a bore shim coil below). Global shim coils are installed, for example, in the area of gradient coils (112x, 112y, 112z), e.g., mostly three or more shim coils to compensate for linear and quadratic terms and possibly also higher-order terms. For example, two shim coil pairs of global shim coils GSC1, GSC2 and GSC3, GSC4 in FIG. 1 may be powered as described in "Second Order Shimming of High Field Magnets" by Siemens Healthcare (http://healthcare.siemens.com/siemens_h-wem-hwem_ssxa_websites-context-root/wcm/idc/siemens_hwem-hwem_ssxa_websites-context-root/wcm/idc/groups/public/@global/@imaging/@mri/documents/download/mdaw/mtqy/~edisp/second_hot_topic_brochure-00017029.pdf) for example. In FIG. 1, shim currents IGSC in the global shim coils are of the same amount and are supplied via a shim cable (e.g., with the current m=4 times IGSC). However, each shim coil may also be supplied individually with power and shim currents ILSC in the local shim coils of the same amount, where each coil is supplied via a shim cable (e.g., with current n=2 times IGSC), where however each shim coil may also be supplied individually with power here.

Global shim coils GSC1, GSC2 and GSC3, GSC4 may be provided for a shim in the direction of the axis z (e.g., longitudinal bore) in FIG. 1 and/or global shim coils for a shim in the direction of the axis x (e.g., horizontal bore) in FIG. 1 and/or global shim coils for a shim in the direction of the axis y (e.g., vertical bore) in FIG. 1.

A second type of shim coil is a local shim coil LSC1, LSC2, e.g., as depicted in FIG. 1 in the (breast-(B)) local coil 106, two local shim coils LSC1, LSC2, or as in the (eddy coils (WS)) local coil 106a two pairs LSC1, LSC2 of local shim coils or more. The local shim coils are attached close to the patient 105, and, for example, may also be part of the RF transmit and/or receive coils (e.g., RX and/or RX, TX) of the local coil(s) 106, 106a.

Local shim coils LSC1, LSC2 may be attached close to the patient 105, for example, within a receive coil or transceiver coil TX, RX, to compensate for strong localized $B_0$ field inhomogeneities, (e.g., in the range of 0-10 ppm and in the area of a region of interest=ROI, such as the breast B in the breast cup B1 of the local coil 106). An advantage of local shim coils LSC1, LSC2 may be that with significantly lower current and setup outlay (e.g., costs), the local inhomogeneities may be compensated for in a better and low-cost way than with "global" shim coils GSC1, GSC2, GSC3, GSC4, which may currently be installed in the gradient coil area for example.

A simultaneous use of global shim coils GSC1, GSC2, GSC3, GSC4 and local shim coils LSC1, LSC2 may deliver good image results, in that the global coils compensate for the large-area $B_0$ field deviations that are caused by the (e.g., MRT basic field) magnets 107 and/or by the patient to be examined 105, and the local shim coils LSC1, LSC2 compensate for spatially-concentrated inhomogeneities.

One question that may be posed is how, during simultaneous use of global shim coils, GSC1, GSC2, GSC3, GSC4 and local shim coils LSC1, LSC2, the MRT system 101 best finds a current setting for the (e.g., possibly different) shim currents (ILSC, IGSC) for all shim coils, which leads to an optimum result or represents a good compromise between algorithmic outlay and results. In addition to the fact that the local shim coil LSC1, LSC2 is a transportable unit, (unlike a global shim coil GSC1, GSC2, GSC3, GSC4), the local shim coil may also distinguish itself from a global shim coil in that the local shim coil is not permanently attached to the magnet on the patient table PTAB.

Nowadays, in accordance at least with the internally known prior art, only global shim coils GSC1, GSC2, GSC3, GSC4 are used in products. For determining the patient an anatomy-individual current setting for shim currents (ILSC, IGSC), a $B_0$ magnetic field map (e.g., mostly 3D $B_0$ magnetic field map and mostly phase map) is recorded for this purpose beforehand. The fields that global shim coils GSC1, GSC2, GSC3, GSC4 generate are known, for example, to the MRT system 101 by a stored description. An algorithm of the MRT 101 may vary the shim currents until such time as a $B_0$ field curve that is as homogeneous as possible is produced from the overlaying of calculated shim field and measured $B_0$ field curve overall. A description of the fields able to be created with a shim coil includes, for example, coefficients of orthogonal sphere functions and/or pixel maps (which specify for example how many (e.g., proportion of magnetic) fields will be created from which shim coil at which point in the chamber as a function of the current in the shim coil).

For an overlaying of fields created with global shim coils GSC1, GSC2, GSC3, GSC4 and fields created with local shim coils LSC1, LSC2, as far as is known internally, there are currently no known dedicated methods that appear to be able to be integrated fully automatically into the clinical workflow.

In one embodiment, in addition to the field description (e.g., stored in field distribution data B-Shim-V-LSC in a memory Sp101) of the (e.g., creatable fields of the) global shim coils GSC1, GSC2, GSC3, GSC4, there is a description stored (e.g., in field distribution data B-Shim-V-LSC) of the (e.g., creatable fields of the) local shim coils LSC1, LSC2.

This description (e.g., in field distribution data B-Shim-V-LSC) may be part of the software in a controller 110, 117 of the MRT-system 101 (e.g., as what is known as a coil file relating to characteristics of the shim coils). The description is retrieved for use of the local shim coil LSC1, LSC2 (and its detection by the MRT), and/or is stored in a digital memory (EEPROM, FLASH etc.) SP-106 of a local coil 106 and/or of the local shim coils LSC1, LSC2 and is retrieved from there by a controller 107 of the MRT 101, for example.

The latter makes possible an individual reconciliation of the shim characteristics of each local shim coil LSC1, LSC2.

For this purpose, the following may be known to a controller 107 of the MRT 101. First, the shim algorithm, for example, may have knowledge of the position Pos (e.g., the position of the center point of the shim coil LSC1, LSC2 in the direction of the axes x, y, z and possibly two angles in space) of one/a number of the local shim coils LSC1, LSC2 (e.g., by laser measurement or as a result of measuring the position of the patient couch with sensors etc.). If the coil type (e.g., breast coil 106 or spine coil 106a) already defines this position Pos in two directions x, y (e.g., since the local coils 106; 106a were rigidly connected to the patient table 104), some of these parameters (e.g., the couch position in the direction of the longitudinal bore axis z) might be sufficient to determine the position Pos relative to the isocenter (e.g., in the center of the FoV) of the basic field magnet 107.

Second, field distribution data (B-Shim-V-GSC, B-Shim-V-LSC) relating to the spatial field distribution may be created in each case by one of the shim coils GSC, LSC1, LSC2 (described above, e.g., as a 3-D field map as a pixel map or coefficient of orthogonal functions (e.g., spherical harmonics) or polynomial coefficients or similar).

Third, global shim coil data (GSC-D and/or LSC-D) may relate to the sensitivity of the shim coil (GSC and/or LSC) to the extent of how much B0 shim magnetic field (e.g., in Tesla) per ampere shim current ILSC, IGSC in a shim coil GSC, LSC1, LSC2 the coil creates, and/or how the fields of the local shim coils LSC1, LSC2 and of the global shim coils GSC1, GSC2, GSC3, GSC4 may be used for a common optimization (e.g., reduction of the $B_0$ inhomogeneity).

For example, in an adjustment measurement, the present $B_0$ field distribution (e.g., as Field map 1=FM1) is measured and an algorithm in a controller (117) may determine suitable shim current settings for the shim currents ILSC, IGSC for the global shim coils GSC1, GSC2, GSC3, GSC4 and the local shim coils LSC1, LSC2.

An adjustment measurement may be done by one of the following approaches, for example.

In one approach, the adjustment measurement may be performed by an orthogonalization approach. In an orthoganlization approach, the 3D field distributions created per unit (e.g., per ampere) of shim current IGSC, ILSC in a shim coil (also referred to here as shim vector (coil) SVc) are measured for the global shim coils GSC1, GSC2, GSC3, GSC4 and the local shim coils LSC1, LSC2 (e.g., as a one-off act in the development of an MRT product) and stored (SP101). Depending on the position Pos of the local shim coils LSC1, LSC2, the field distribution able to be created by the coils is taken into consideration during the actual imaging measurement on the patient (e.g., as a displacement of the field distribution in accordance with the position in direction z before orthogonalization). The field distributions SVc are orthogonalized (SVo), such that the field distributions represent the basic vectors of the possible shim space. The orthogonalized field distributions SVo are thus, so-to-speak, virtual shim coils that are described as a linear combination of the real shim coils. The field error caused by a patient 105, etc. (e.g., by changing the field $B_0$ that is to be corrected with a shim) is determined by an MR method. This field error is mapped by an orthogonal projection onto the field distribution SVo. This directly gives the shim current that is necessary in the virtual shim coil. The shim current is converted to real shim currents in that the previously determined linear combination from the orthogonalization (in act 2 above) is accordingly applied inversely.

In a second approach, the adjustment measurement may be performed by an overall optimization approach. In an overall optimization approach, the fields of the local shim coils LSC1, LSC2 and the global shim coils GSC1, GSC2, GSC3, GSC4 may be completely added (e.g., 3D=three-dimensional) in a linear combination. In an optimization method (such as, e.g., least squares), a setting is sought that compares shim currents IGSC, ILSC and the fields resulting therefrom with the measured $B_0$ field and sets them so that the $B_0$ inhomogeneity is minimized (by the shim).

In a third approach, the adjustment measurement may be performed by a step by step approach. In a step by step approach, wide-area inhomogeneities are rectified by global shim coils GSC1, GSC2, GSC3, GSC4, and shim currents are calculated for the local shim coils LSC1, LSC2. In one variant of a step by step approach, the shim currents of the global shim coils GSC1, GSC2, GSC3, GSC4 are calculated. The fields of this global shim coil GSC1, GSC2, GSC3, GSC4 setting are overlaid with the measured fields. This produces a new field map (FM2). In another act, this field map is used in order to find the optimum setting of the local shim coils LSC1, LSC2. In a second variant of a step by step approach, as above, only that the field map FM2 is applied by setting the currents of the global shim coils GSC1, GSC2, GSC3, GSC4 and the second field map FM2 is obtained from a new measurement. This measurement, as above, may cover a 3D volume, but possibly only includes of one or of a few slices, in order to accelerate the process. The choice of slice for the measurement is to be configured to the volume to be shimmed (e.g., in the back of the neck only one sagital slice instead of complete 3D measurement).

In a fourth approach, the adjustment measurement may be performed by a blind search with N measurements. In a blind search approach, the currents of the global shim coils GSC1, GSC2, GSC3, GSC4, are calculated from the first field map (which may be referred to as FM1). Thereafter, a number of field maps (N) with different settings of the currents ILSC of the local shim coils (e.g., from minimum to maximum current) are measured. To accelerate these multiple measurements in such cases, the measurement of a low-resolution 3D area or of an individual slice or of a few slices may be sufficient. Thereafter, a shim current ILSC, which delivers the best optimization result, is calculated from the N field maps.

In a fifth approach, the adjustment measurement may be performed by a targeted optimization. In a targeted optimization approach, the shim currents IGSC of the global shim coils GSC1, GSC2, GSC3, GSC4 are calculated from the first field map. Thereafter a number of field maps (N) with different settings of the LSC1, LSC2 currents are measured. To accelerate these multiple measurements in such cases, a low-resolution 3D region or an individual slice or a few slices may suffice. Unlike in the blind search approach, which searches the entire dynamic range of LSC1, LSC2 and interpolates therefrom (e.g., linearly), a targeted optimization algorithm searches by variation for a minimum $B_0$ inhomogeneity and stops the recording of new field maps when this minimum has been found.

In certain embodiments, the above described approaches may converge if the global shim coils GSC1, GSC2, GSC3, GSC4 or the local shim coils LSC1, LSC2 or both are already occupied beforehand with shim currents IGSC, ILSC during the measurement of the first Field Map FM1. Such a convergence may improve inhomogeneities in the anatomical region concerned (e.g., fix the empirically determined value for specific anatomy/coil) and thus bring the start point of the optimization with the first Field Map FM1 closer to the optimum point. To this end, the currents of the global shim coils GSC1, GSC2, GSC3, GSC4 and local shim coils LSC1, LSC2 may be preset for specific anatomy. This may especially be an advantageous approach for the local shim coils LSC1, LSC2.

In certain embodiments, the above described approaches may include one of the following.

For one, the approaches may include a sub-adjustment of shim volumes. In the algorithm system, it may be advantageous to optimize the shim fields of the local shim coils LSC1, LSC2 only to a part of the total shim volume. Large shim volumes (e.g., relative to the size of the local shim field) regions may arise where a local shim coil LSC1, LSC2 barely contributes to the field and the optimization may possibly be carried out incorrectly, if a plurality of points are included in the optimization, where the local shim coils LSC1, LSC2 only generate little field. Therefore, it may be sensible to divide the total shim into sub volumes and only optimize the local shim fields via a "sub volume." A sub volume may be defined by the parameters of the local shim coil LSC1, LSC2 itself (e.g., in the coil file) or may be calculated automatically by regions being filtered out that have low field proportions.

Second, the approaches may include a "current limit is reached" approach. If the maximum current level has been reached for a local shim coil LSC1, LSC2 it may be advantageous to design the algorithm so that an attempt is made, with a new shim current setting, to find an LSC1, LSC2 setting that does not come up against the maximum current limit.

At the end of each method described above, there may be a verification act, which in a part FoV (e.g., small 3D volume or one or a few slices) compares the measured with the calculated $B_0$ field. For a good match, the measurement continues. For a bad match, user interaction may take place (e.g., warning, query) or the measurement may be started again (e.g., with other start parameters for the shim currents).

Thus one (or more) local shim coil(s) LSC1, LSC2 may be combined with the built-in shim coil system consisting of GSC1, GSC2, GSC3, GSC4 of an MRT 101. In this case, the built-in shim coils GSC1, GSC2, GSC3, GSC4 may be a system suitable for all regions of the body B, WS of a patient 105. The local shim coils LSC1, LSC2 are optimized, for example, to the inhomogeneities caused by the body shape (3D susceptibility distribution). A spine coil WS and/or a neck coil may unlikely be used for breast examinations. A local shim coil LSC1, LSC2 may contain a number of channels, but may, as a result of the already existing homogenization by the built-in (global) shim coils, only correct the remaining variance of the different test samples. Through this and through a position directly on the patient 105, the power requirement may be reduced and complex field profiles may be achieved.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance tomography (MRT) system comprising:
   a shim system comprising:
      at least one global shim coil in an area surrounding a bore of the magnetic resonance tomography system;
      at least one local shim coil in a local coil of the magnetic resonance tomography system; and
   a shim controller configured to determine global shim currents for the global shim coil and local shim currents for the local shim coil,
   wherein the shim controller is configured to determine the global shim currents and the local shim currents using a three-dimensional linear combination of shim fields created with the at least one global shim coil and the at least one local shim coil with an optimization method for searching for a minimization of the basic field inhomogeneity caused by the shim currents of the at least one global shim coil and the at least one local shim coil.

2. The magnetic resonance tomography system as claimed in claim 1, wherein the shim system comprises a plurality of global shim coils in the area surrounding the bore, a plurality of local shim coils in the local coil, or a plurality of global shim coils in an area surrounding the bore and a plurality of local shim coils in the local coil.

3. The magnetic resonance tomography system in claim 1, further comprising:
   a global shim coil memory comprising global shim coil data relating to shim characteristics of the at least one global shim coil, field distribution data relating to a spatial field distribution of a shim field, or a combination thereof;
   a local shim coil memory comprising local shim coil data relating to shim characteristics of the at least one local shim coil, field distribution data relating to a spatial field distribution of a shim field created with the at least one local shim coil, or a combination thereof; or
   a combination thereof,
   wherein the shim controller is configured to determine the global shim currents and the local shim currents using the global shim coil data and the local shim coil data.

4. The magnetic resonance tomography system as claimed in claim 1, wherein the at least one global shim coil, the at least one local shim coil, or both the at least one global shim coil and the at least one local shim coil are configured to provide field distribution data relating to a spatial field distribution of a shim field,
   wherein the field distribution data is stored outside the local coil.

5. The magnetic resonance tomography system as claimed in claim 1, wherein the at least one local shim coil is configured to provide field distribution data relating to a spatial field distribution of a shim field,
   wherein the field distribution data is stored in a memory in the local coil.

6. The magnetic resonance tomography system as claimed in claim 1, wherein the shim controller is configured to determine the global shim currents and the local shim currents using: (1) the local shim coil position data representing a position of the local shim coil; (2) data representing a type of the local shim coil; or (3) both the local shim coil position data representing the position of the local shim coil and the data representing the type of the local shim coil.

7. The magnetic resonance tomography system as claimed in claim 1, wherein the at least one global shim coil, the at least one local shim coil, or both the at least one global shim coil and the at least one local shim coil are configured to provide field distribution data relating to a spatial field distribution of a shim field,
wherein the spatial field distribution is provided as a three-dimensional field map, as a pixel map, or as coefficients of functions.

8. The magnetic resonance tomography system as claimed in claim 1, wherein global shim coil data, local shim coil data, or global shim coil and local shim coil data specify a sensitivity of at least one shim coil by how much magnetic field is able to be created per ampere of shim current in the at least one shim coil.

9. The magnetic resonance tomography system as claimed in claim 1, wherein the shim controller is configured to determine the global shim currents and the local shim currents: (1) using a stored $B_0$ field distribution of a basic field previously created by a basic field magnet of the MRT alone; (2) without field generation by shim coils determined in an adjustment measurement; or (3) using the stored $B_0$ field distribution of the basic field and without field generation by shim coils determined in the adjustment measurement.

10. The magnetic resonance tomography system as claimed in claim 1, wherein the shim controller is configured to determine the global shim currents and the local shim currents using stored shim field strengths created for the global shim coil and the local shim coil measured per unit of shim current.

11. The magnetic resonance tomography system as claimed in claim 1, wherein the shim controller is configured to determine the global shim currents and the local shim currents using a field distribution of a shim field created with the local shim coil through the shim current and position data representing a position of the local shim coil.

12. The magnetic resonance tomography system as claimed in claim 1, wherein the shim controller is configured to determine the global shim currents and the local shim currents using field distribution data representing a field distribution of a shim field created with the local shim coil by the shim current,
wherein the shim field for a shim coil comprises three files in each case,
wherein each file represents field distribution data relating to a field distribution in the direction of one of three base vectors orthogonal to one another of a shim space and as a linear combination together represents the field distribution of a shim field able to be created with the shim coil.

13. The magnetic resonance tomography system as claimed in claim 1, wherein the shim controller is configured to determine the global shim currents and the local shim currents using stored data relating to a field error created by a patient to be examined, representing a change of the basic field.

14. The magnetic resonance tomography system as claimed in claim 13, wherein the stored data comprises three files,
wherein each file represents field distribution data relating to a change of the field distribution in the direction of one of three base vectors, orthogonal to one another of a possible shim space and as a linear combination together represents the change of the field distribution of the basic field.

15. The magnetic resonance tomography system as claimed in claim 1, wherein the global shim currents are defined for the global shim coil in order to reduce large-area inhomogeneities, and
wherein a new field map is determined that takes account of shim fields created by the global shim currents in the global shim coil and a basic field inhomogeneity caused by a patient to be examined and the basic field, and the local shim currents are defined for the local shim coil.

16. The magnetic resonance tomography system as claimed in claim 15, wherein the new field map takes account of the shim fields only in the area of the patient to be examined.

17. The magnetic resonance tomography system as claimed in claim 1, wherein the shim controller is configured to determine the global shim currents from a $B_0$ field distribution, determined in an adjustment measurement, of a basic field created by basic field magnets of the MRT alone, without field generation by shim coils, or by the basic field magnets of the MRT and without field generation by shim coils, and
wherein a number of field maps with different settings distributed over possible ranges of the local shim currents in the local shim coil are measured in the Field of View or a slice or a number of slices of a region of interest in each case, after which the local shim currents in the local shim coil are selected for which a measured field error representing a change of the basic field is minimal or which is produced by an optimization.

18. The magnetic resonance tomography system as claimed in claim 1, wherein the shim controller is configured to determine the global shim currents from a $B_0$ field distribution, determined in an adjustment measurement, of a basic field created by a basic field magnet of the MRT alone, without field generation by shim coils, or by the basic field magnets of the MRT and without field creation by shim coils, and
wherein a number of field maps with different settings of the local shim currents in the local shim coil are measured in the Field of View or a slice or a number of slices of a Point Of Interest in each case until a minimum is produced, after which those shim coil currents in the local shim coil are selected for which a measured field error representing a change of the basic field is minimal or which is produced from an optimization.

19. The magnetic resonance tomography system as claimed in claim 1, wherein the shim controller is configured to determine the global shim currents from a $B_0$ field distribution, determined in an adjustment measurement, of a basic field created by a basic field magnet of the MRT alone, without field generation by shim coils, or by the basic field magnets of the MRT and without field creation by shim coils,
wherein the global shim coil, the local shim coil, or the global shim coil and the local shim coil are pre-equipped during measurement of the $B_0$ field distribution with shim currents.

20. The magnetic resonance tomography system as claimed in claim 1, wherein the shim controller is configured to determine the global shim currents and the local shim currents in that a shim field of the local shim coil is only optimized to at least one part of the total shim volume, and is stored or is calculated automatically, in that regions having small field proportions are filtered out.

21. The magnetic resonance tomography system as claimed in claim 1, wherein the shim controller is configured to determine the global shim currents and the local shim currents in that a number of field maps with different settings distributed over the possible range of the required shim currents in the local shim coil in the Field of View in each case or a slice or a number of slices of a point of interest are measured, and when the maximum current limit has been reached for a local shim current, an attempt is made, with a new global shim current setting, to find a local shim coil setting that is less than a maximum permissible current limit.

22. The magnetic resonance tomography system as claimed in claim 1, wherein the shim controller is configured to determine the global shim currents and the local shim currents using an iterative measurement process wherein a measured $B_0$ field is compared with a calculated $B_0$ field in a part of the Field of View, and, if there is a match, the measurement continues, and if there is a bad match, a query is generated or the measurement is started again with other start parameters for the shim currents.

23. The magnetic resonance tomography system as claimed in claim 1, wherein the at least one local shim coil is provided in one or more of the following areas: (1) an area of a local coil of the magnetic resonance tomography system; (2) as part of radio-frequency transmit antennas of a local coil; or (3) in a patient couch.

24. The magnetic resonance tomography system as claimed in claim 1, wherein the shim controller takes into consideration a type of a local coil with respect to a body region to be examined by the local coil connected, detected, or connected and detected in the magnetic resonance tomography system, a patient couch, or the magnetic resonance tomography system and the patient couch.

25. The magnetic resonance tomography system as claimed in claim 1, wherein at least one global shim coil, the at least one local shim coil, or the at least one global shim coil and the at least one local shim coil are also either gradient coils for creating a gradient field or RF transmit, RF receive, or RF transmit and receive coils for creating a radio-frequency field.

26. The magnetic resonance tomography system as claimed in claim 1, further comprising at least one gradient coil, a local coil for creating a gradient field, or at least one gradient coil and a local coil for creating a gradient field.

27. The magnetic resonance tomography system as claimed in claim 1, wherein at least one global shim coil is a shim coil arranged radially outside the bore of the MRT system, a shim coil arranged radially outside the housing jacket of the bore of the MRT, an MRT housing shim coil, or a combination thereof.

* * * * *